(12) United States Patent
Wild

(10) Patent No.: US 8,097,004 B2
(45) Date of Patent: Jan. 17, 2012

(54) APPARATUS FOR DISPENSING SURGICAL CLIPS

(75) Inventor: Andrew Michael Wild, London (GB)

(73) Assignee: Teresa Kathleen Wild, Jeddah (SA), part interest ( * ) Notice: Subject to any disclaimer, the term of this patent is extended or adjusted under 35 U.S.C. 154(b) by 1118 days.

(21) Appl. No.: 11/575,289

(22) PCT Filed: Sep. 14, 2005

(86) PCT No.: PCT/GB2005/003542
§ 371 (c)(1),
(2), (4) Date: Aug. 28, 2007

(87) PCT Pub. No.: WO2006/030204
PCT Pub. Date: Mar. 23, 2006

(65) Prior Publication Data
US 2008/0046006 A1    Feb. 21, 2008

(30) Foreign Application Priority Data

Sep. 14, 2004   (GB) .................................. 0420505.0

(51) Int. Cl.
*A61B 17/068* (2006.01)
(52) U.S. Cl. ......... 606/142; 606/139; 606/143; 606/151
(58) Field of Classification Search .................. 606/139, 606/142–143, 151, 153, 157–158; 227/175.1, 227/177.1, 19, 902
See application file for complete search history.

(56) References Cited

U.S. PATENT DOCUMENTS

| | | | |
|---|---|---|---|
| 5,047,038 A | 9/1991 | Peters et al. | |
| 5,171,249 A | 12/1992 | Stefanchik et al. | |
| 5,868,759 A | 2/1999 | Peyser et al. | |
| 6,352,541 B1 * | 3/2002 | Kienzle et al. | ................ 606/143 |

(Continued)

FOREIGN PATENT DOCUMENTS

EP        0774237 A    5/1997

(Continued)

*Primary Examiner* — Corrine M McDermott
*Assistant Examiner* — Mark Mashack
(74) *Attorney, Agent, or Firm* — Hovey Williams LLP

(57) ABSTRACT

An apparatus is described for dispensing a surgical clip (1) of memory metal, the clip being of the kind having a central portion (2) defining a plane and a pair of limbs (3, 4) extending from opposite sides of the central portion, one (3) of the pair of limbs having a free end disposed forward, and above the plane, of the central portion (2) and the other (4) of the pair of limbs having a free end disposed forward, and below the plane, of the central portion (2). The apparatus comprises an inner shaft (27) in which the clip (1) can be mounted and an outer movable member (25) for displacing the clip along the longitudinal axis of the inner shaft (27). The inner shaft comprises a central region (40) for accommodating the central portion (2) of the clip and a pair of diagonally opposed guide rails (41, 42) provided on opposite sides of the central region (40), one (41) of the guide rails being positioned above the central region to accommodate the one limb (3) and the other (42) of the guide rails being positioned below the central region to accommodate the other limb (4) of the clip. The rails hold the limbs of the clip splayed even though at room temperature they are biased into their clamping configuration, and the clip can then be applied round a body passageway from the end of the shaft (27).

29 Claims, 9 Drawing Sheets

U.S. PATENT DOCUMENTS

| | | | |
|---|---|---|---|
| 6,520,972 B2 * | 2/2003 | Peters | 606/143 |
| 6,607,542 B1 * | 8/2003 | Wild | 606/157 |
| 7,056,330 B2 * | 6/2006 | Gayton | 606/219 |
| 2002/0062130 A1 * | 5/2002 | Jugenheimer et al. | 606/142 |
| 2002/0082618 A1 | 6/2002 | Shipp et al. | |
| 2002/0099388 A1 * | 7/2002 | Mayenberger | 606/139 |
| 2003/0109890 A1 * | 6/2003 | Kanner et al. | 606/142 |
| 2003/0233105 A1 * | 12/2003 | Gayton | 606/142 |
| 2004/0236355 A1 * | 11/2004 | Anthony et al. | 606/142 |
| 2004/0249398 A1 * | 12/2004 | Ginn | 606/151 |
| 2005/0107871 A1 * | 5/2005 | Realyvasquez et al. | 623/2.11 |
| 2006/0085015 A1 | 4/2006 | Whitfield et al. | |

FOREIGN PATENT DOCUMENTS

| | | |
|---|---|---|
| GB | WO 00/35355 | 6/2000 |
| GB | PCT/GB2004/001060 | 9/2004 |
| WO | PCT/US2002/20866 | 1/2003 |

* cited by examiner ered on the shape-memory material, such that the clip can be stored in the

APPARATUS FOR DISPENSING SURGICAL CLIPS

This is the United States National Stage of Patent Cooperation Treaty Application No. PCT/GB05/003452 filed Sep. 14, 2005, which claims priority to United Kingdom Patent Application No. 0420505.0 filed Sep. 14, 2004.

FIELD OF THE INVENTION

The present invention relates to an apparatus for dispensing surgical clips, and in particular to an apparatus or applicator for applying surgical clips to body passageways, such as blood vessels or ducts, which are to be occluded or encircled.

BACKGROUND OF THE INVENTION

Surgical clips are known which are designed to permanently or temporarily occlude body passageways, and may be used in procedures including the surgical closure of veins and arteries for haemiostasis; ligation; vascular occlusion; occlusion of congenital or aberrant cardiac vessels; the occlusion of body ducts for sterilisation or prior to resection; intracranial vessel occlusion for neurosurgery; occlusion of aberrant vessels or aneurysms; and occlusion of arterio-venous malformations. A general principle is that such clips close the body passageway by gripping, without puncturing the tissue.

Various designs of surgical clip are known, including the Hem-o-lok ligating clip available from Weck Closure Systems and the Yasargil-Phynox clip available from Aesculap. The Hem-o-lok clip has a hinged plastic jaw comprising two jaw members with cooperating snap-fit closure formations, and is applied by a simple pliers-like applicator which closes the open jaw members together across the blood vessel to be occluded. The Yasargil-Phynox clip has a hinged metal jaw with a self-closing bias. Application of this clip is performed using a simple pliers-like applier, by prising the jaw members apart across the blood vessel to be occluded and then releasing the applier so that the jaw members spring together.

In each of these cases, in order to actuate the loaded applier the surgeon must make available the whole of his dominant hand, because of the pliers-grip hand action required. Furthermore, in each case, each clip must be loaded onto the applier manually and individually in the open condition.

In WO-A-00/35355, the disclosure of which is incorporated herein by reference, there is disclosed surgical clips having first and second ends and an intermediate central portion. The ends are preferably legs which extend in generally the same direction in a first (open) configuration of the clip, to allow the body passageway to be received in the clip. The clip is constructed so that the ends can close towards the central portion under an inherent biassing force into a second (closed) configuration so that the body passageway is then gripped by the clip. The inherent biassing force can be provided by use of a temperature-dependent shape memory material for the construction of the clip, and by arranging for the clip to experience a temperature change when the change from the first to the second configuration is desired. This temperature change can be a rise in temperature as a result of the clip being introduced into an operating zone within a patient's body.

WO-A-00/35355 also discloses two applicators for applying the clips. One of these comprises a shaft for holding the clips, the shaft having a first, proximal end connected to a handle and trigger and a second, distal end provided with a port through which the clips are dispensed. The clips are held in sequence in the shaft and are advanced along the shaft towards the distal end by a spring biased pressing rod. The clips to be loaded into the applicator each comprise a central elongate element having two enlarged ends, forming a shape resembling that of a weightlifter's dumbbell. The clips are loaded end-to-end in the shaft of the applicator.

In use, the port of the applicator is positioned over the vessel to be occluded, and the clips are advanced along the shaft until the foremost clip is positioned over the vessel. Once the foremost clip is in contact with the vessel, the clip warms up to body temperature, and as it does so it deforms into its second configuration and encircles the vessel.

A second applicator disclosed in WO-A-00/35355 is generally similar, but the clips housed in the apparatus are maintained at a low temperature by a temperature control device.

More recently, I have modified the shape of the prior art surgical clip to improve the occlusion performance. A version of the modified clip is shown in FIG. 1 of the accompanying drawings. The present invention relates particularly, though not exclusively, to an applicator for applying surgical clips of this type.

Referring to FIG. 1, a clip 1 of this type is generally planar with a central (main) portion 2 and a pair of resilient limbs 3, 4 each extending from the central portion of the clip so that the free ends project in a generally similar forward direction. The stems of the limbs preferably extend in opposite lateral directions from the central portion and then curve round towards their free ends into the forward direction. The central portion of the clip comprises a base portion 5 and a reaction or counter-surface portion 6, the reaction portion being connected to the base portion 5 and defining a reaction surface 7. The reaction surface is preferably elongate, in the lateral direction, and is preferably substantially fixed in relation to the movement of the limbs from a first, open, configuration to a second, closed, configuration. The connection between the base portion and the reaction portion of the clip is preferably via a neck portion, which is preferably narrow in relation to at least the reaction portion.

The clip 1 is preferably generally planar but with the respective planes of the parts offset somewhat against one another. In particular, the plane of the reaction portion 6 may be at an angle (e.g. up to 30°) to the plane of the base portion 5, with a corresponding twist provided at the region of connection between the two portions. Preferably also, one limb 3 lies to one side of (e.g. above) the plane of the base portion, and the other limb 4 lies to the opposite side of (e.g. below) that plane.

FIG. 1 shows such a clip in its resting configuration at room temperature. In this configuration, the limbs can be splayed (stressed) apart to an open configuration within the maximum recoverable stress of the material, and a bias towards the closed condition can be provided, e.g. using shape-memory materials. When the clip is applied in its open configuration to a body passageway, from an applicator, the limbs 3, 4 of the clip move under an inherent biassing force from the open configuration to the closed configuration. In the closed configuration, the free ends 8, 9 of the limbs overlie each side of (above and below) the reaction portion 6, gripping the passageway to be occluded in the plane of the clip and thus providing an efficient and secure occlusive effect. In order to provide the necessary closing force, the clip is preferably made from a stress-dependent and/or temperature-dependent shape-memory material, such that the clip can be stored in the open configuration under a certain stress and at a temperature below body temperature, but will move to the closed configuration when the stress is released and/or the temperature raised (e.g. when introduced into an operating zone within a patient). A suitable material is nitinol.

As shown in FIG. 1, the base portion 5 of the clip is preferably constructed in a plurality of sections (e.g. two halves) mutually linked by one or more region of weakness which can easily be cut to release the clip from the body passageway after use.

For further details of the construction of this type of clip, please see my International (PCT) Patent Application No. PCT/GB2004/001060, the contents of which are incorporated herein by reference. I have found that the modified clip arrangement described and claimed in that PCT patent application and illustrated in FIG. 1 of the accompanying drawings provides a remarkable and useful gripping and occlusive action on a wide range of body passageways.

Previous applicators for clips of this general type, such as those of WO-A-00/35355 mentioned above, are not suitable for the particular improved clip arrangement described above.

It is an object of the present invention to provide an applicator whereby the clips in the improved arrangement described above can be held before use and then individually dispensed to close onto and occlude a body passageway in a controlled and simple manner by a surgeon.

BRIEF DESCRIPTION OF THE INVENTION

According to a first aspect of the present invention, there is provided an apparatus for dispensing a surgical clip, the clip comprising a central portion defining a plane and a pair of limbs extending from opposite sides of the central portion, one of the limbs having a free end disposed forward, and above the plane, of the central portion and the other of the limbs having a free end disposed forward, and below the plane, of the central portion, the apparatus comprising:

an inner shaft in or on which the surgical clip can be mounted with its limbs facing forwards; and an outer movable member for displacing the surgical clip along the longitudinal axis of the inner shaft;

wherein the inner shaft comprises a central region for accommodating the central portion of the surgical clip, and a pair of opposed (preferably diagonally opposed) guide rails provided on opposite sides of the central region, one of the guide rails being positioned above the central region to accommodate the one limb and the other of the guide rails being positioned below the central region to accommodate the other limb of the surgical clip.

According to a second aspect of the present invention, there is provided an apparatus according to the first aspect, when loaded with one or more surgical clip of the type defined.

The clip is constructed such that the limbs are resilient or inherently biassed to close on application of an appropriate triggering event. Such closure will move the limbs from the forwards orientation towards the central portion, whereby a body passageway located within the clip is gripped and occluded between the limbs and the central portion. The triggering event may, for example, be release of the stress under which the clips are held, a rise in temperature, or both.

The expression "resilient" and like expressions used herein shall be taken to refer to all forms of inherent or internal (molecular) biassing of the relevant portions of the clip towards its second (closed) configuration. For example, a biocompatible temperature-responsive and/or stress-responsive shape-memory material can be used.

The clip may suitably be integrally formed of a superelastic or pseudoelastic shape-memory material. The material may preferably be a temperature-dependent shape-memory material. Further details of such materials are given in WO-A-00/35355. The clip may suitably be integrally formed from sheet nitinol metal (nickel-titanium alloy). The closed condition of the clip represents the austenitic phase of the nitinol; the resting condition of the clip represents the martensitic phase, and in this phase the material will tolerate an applied stress within the maximum recoverable stress. This stress can be applied by the applicator, by virtue of the forced splaying of the limbs of the clip into the open condition for dispensing from the applicator.

The rails are thus preferably arranged to hold the limbs of the clip splayed and under a certain stress within the maximum recoverable stress of the clip material. The clip material is resilient so that, when the clip is so held in the apparatus, the limbs are maintained open against the inherent restoring bias. The clips can also desirably be held at a temperature somewhat below body temperature. On release from the apparatus, the limbs close onto a body passageway under the effect of the resilient closing force induced and/or released by the release of the stress and/or the rise in temperature.

In the open condition, the limbs preferably extend laterally outwards from the said opposite sides of the central portion of the clip and then turn forwards so that in the open condition of the clip the free ends of the limbs are disposed in a generally similar forwards direction. In the resting condition, the limbs are slightly more inturned towards each other, i.e. less splayed apart. For convenience, both orientations will be referred to herein as "the generally forwards direction".

The central portion of the clip preferably comprises a base portion and a reaction portion, which may suitably be elongate in the lateral direction, mounted to the base portion, preferably via a connecting region and most preferably via a neck which is suitably narrow in relation to at least the reaction portion. The reaction portion defines a generally forwardly directed reaction surface disposed between the base portion and the free ends of the limbs.

The reaction surface and the limbs are suitably dimensioned and arranged so that in the closed condition of the clip substantially the entire transverse width of the occluded body passageway is in contact with the reaction surface. At least one of the opposed cooperating parts of the central portion (e.g. the reaction surface) and the limbs may be provided with surface projections—for example, rounded teeth, pointed teeth, nipping heads, or any combination thereof—which serve in use to enhance grip of the clip on the body passageway.

The limbs may be connected to the central portion of the clip via a curved portion of the limb having a connection point to the central portion behind the reaction portion of the clip. A further curve of opposite direction may suitably be provided in each limb, in order to curve the limb so that its free end is disposed forwards of the base portion. An elongate portion may be present in each limb between the curves, whereby during closure a leverage effect is produced on that part of the limb which is in contact with the body passageway.

The base portion of the clip is preferably constructed in the form of an open loop or generally U shaped member having a closed end directed away from the limbs and an open end at which the limbs and the reaction portion are connected to the base portion. The base portion may, in particular, be provided as a plurality of sections (e.g. two halves), preferably mutually linked by one or more region of weakness which can easily be cut to release the clip from the body passageway after use. The reaction surface will then typically also be provided in two halves, each of which may be connected to one side of the open end of the base portion via a neck region, the two halves being complimentarily juxtaposed to define the reaction surface of the clip For further details of the construction of this type of clip, see International (PCT) Patent Application No. PCT/GB2004/001060.

With the surgical apparatus (applicator) according to this aspect of the invention, the surgical clip can be advanced through the shaft of the applicator in a regulated manner at room temperature, despite the considerable natural closing force of the limbs of the surgical clip, because the guide rails hold the clip open until it exits (is dispensed from) the end of the shaft.

The clips are intended to lie in or on the shaft, with the free ends of their limbs facing forwards and the plane of the clips generally parallel to the shaft axis. "Forwards" thus means "in the direction of the dispensing end (hereafter 'release zone') of the applicator"; "above" and "below", of course, are arbitrary designations.

BRIEF DESCRIPTION OF THE DRAWINGS

For a better understanding of the invention, embodiments will now be described with reference, by way of example only, to the accompanying drawings, in which.

DETAILED DESCRIPTION OF THE DRAWINGS

Figure 1:
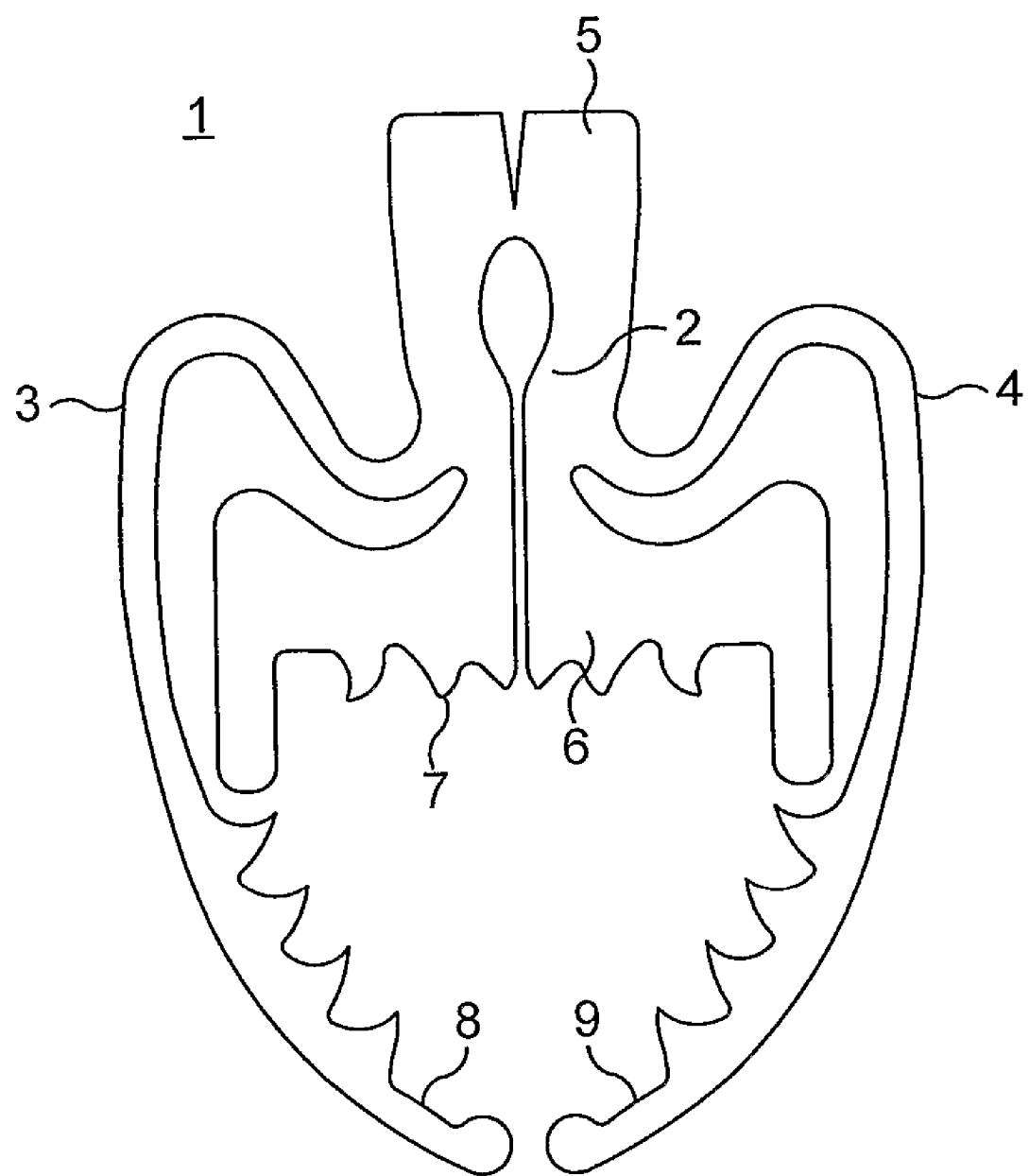
FIG. 1 shows a surgical clip (in the open configuration) of the general type relevant to the present application.

Referring to the drawings, FIG. 1 has already been described above.

Figure 2:
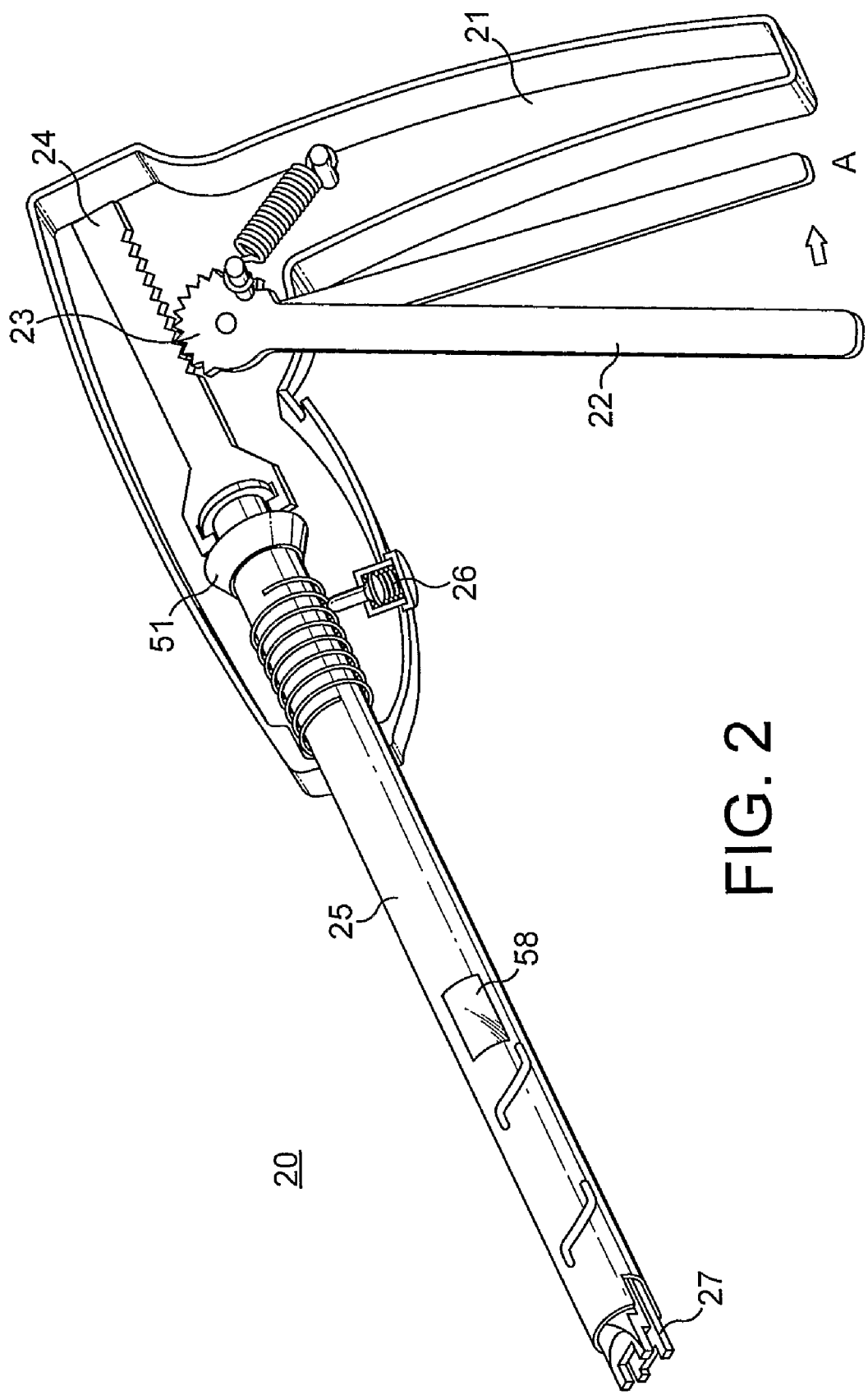
FIG. 2 shows the overall construction of an applicator according to an embodiment of the invention.

FIG. 2 shows the overall construction of an applicator 20 according to an embodiment of the invention. The applicator comprises a hand grip 21, a trigger 22 (shown in two positions in the Figure), a cog 23 and a ratchet 24, an outer sliding tube 25, a sprung stop-cap 26 and an inner shaft 27. The components of the applicator are preferably made from a medical grade polymer, such as Delrin™.

Figure 13:
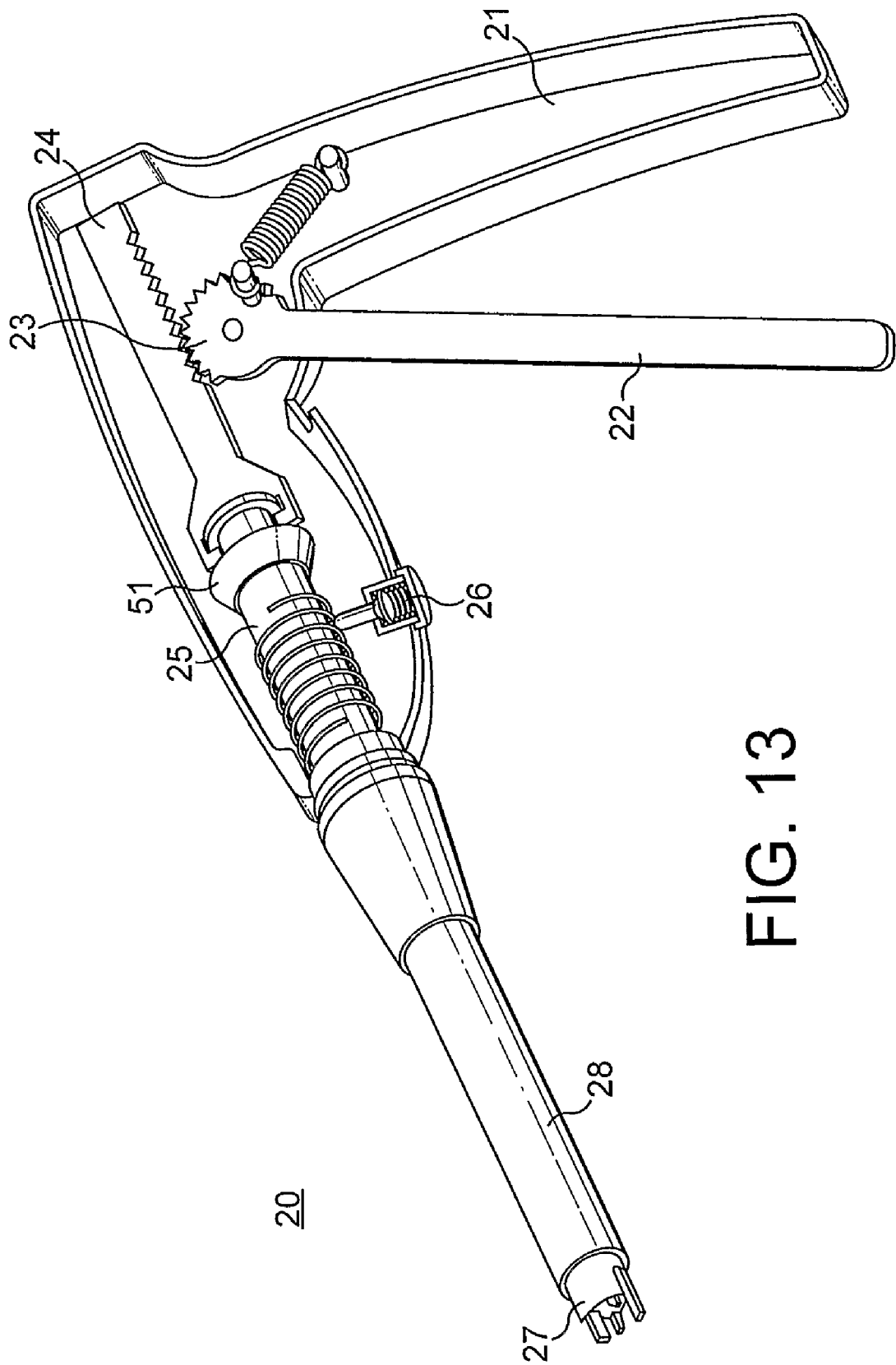
FIG. 13 shows the casing provided around the outer sliding tube and inner shaft of the applicator.

The inner shaft 27 of the applicator 20 is capable of being loaded with a small number of clips 1, and is provided within the outer sliding tube 25 of the applicator. The outer sliding tube is used to advance the clips along the applicator in sequence, upon actuation of the trigger 22. A casing 28 may be provided around the inner shaft 27 and the outer sliding tube 25, as shown in FIG. 13.

Figure 3:
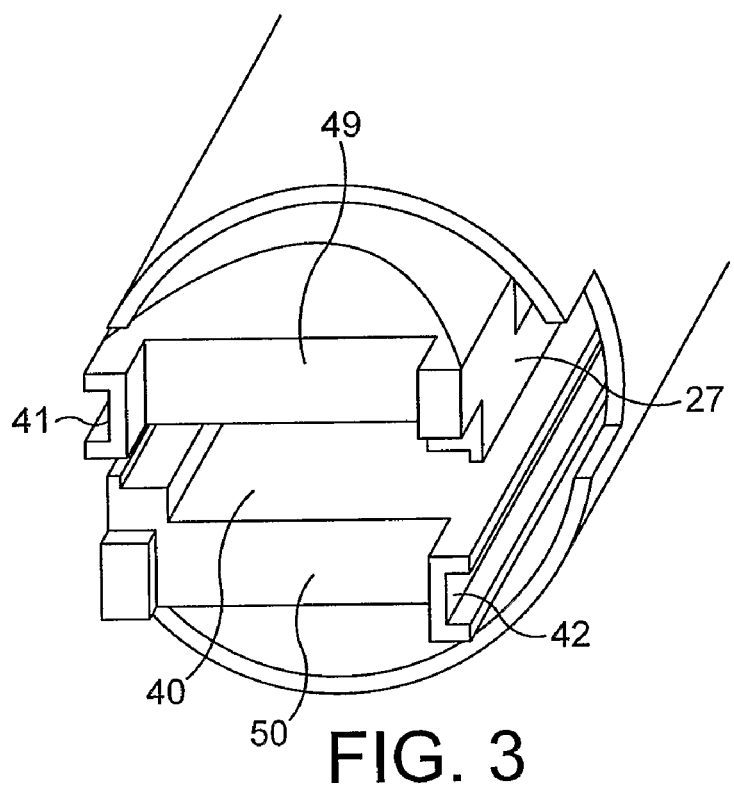
FIG. 3 shows a perspective view of an inner shaft of the applicator of FIG. 2.

FIG. 3 shows a perspective view of the inner shaft 27 (slide rail) of the applicator according to FIG. 2. The inner shaft shown in FIG. 3 comprises two substantially identical longitudinal parts 49, 50 in the form of spaced bars defining a central region (carriage) 40 for accommodating the reaction portion 6 (central die) and base portion 5 (head) of each of the loaded clips 1. To one side of the central region 40 and above it, there is provided a first guide rail 41, constituted by a channel in one side of the upper bar 49. On the opposite side of the central region 40 and below it, there is provided a similar, second guide rail 42. Thus, the first and second guide rails 41, 42 are provided on the outer surface of the inner shaft 27 and are diagonally opposed, forming a pair of inverted, outwardly facing channels. This is due to the lower bar 50 substantially being a rotation of the upper bar 49 through 180° about the central, longitudinal axis of the inner shaft 27.

Due to the off-set arrangement of the limbs 3, 4 of each of the clips 1, with one limb 3 tending to close in front of (above), and the other limb 4 behind (below), the plane of the central die 6, each clip has a natural closing torque or rotational moment. In order to apply a clip effectively, it is essential that this rotational moment is suitably controlled, particularly during clip advance; otherwise, the clip will twist and spring off the mechanism.

The opposed (inverted) guide rails 41, 42 of the inner shaft 27 of the applicator enable this rotational moment to be controlled, and thus allow the clips to be advanced along the applicator in a regulated manner. Each guide rail 41, 42 holds one of the limbs 3, 4 of each clip, and by providing the guide rails in this configuration, the offset configuration of the limbs of each of the clips is naturally accommodated, with one limb 3 being guided by the upper guide rail 41 and the other limb 4 being guided by the diagonally opposed, lower guide rail 42. The limbs of each clip point forwards along their respective guide rails, towards the release zone 43 of the applicator.

Each of the guide rails 41, 42 is shaped as a groove running longitudinally along the outside of its bar 49, 50 forming the inner shaft 27, and preferably has a substantially rectangular cross-section which is enclosed on three sides. The double rail and front aperture (release zone) arrangement therefore control both clockwise and anticlockwise moments about the horizontal axis, and the clip is held horizontal until final release.

In order to allow the limbs of the clips to slide easily along the guide rails, the inner surfaces of the guide rails may be coated with a material which decreases the friction between the limbs of the clips and the guide rails. Titanium is particularly suitable, as this will not contaminate the clip feet with extraneous metals, which could accelerate clip corrosion after implantation in the human or animal body.

Figure 4:
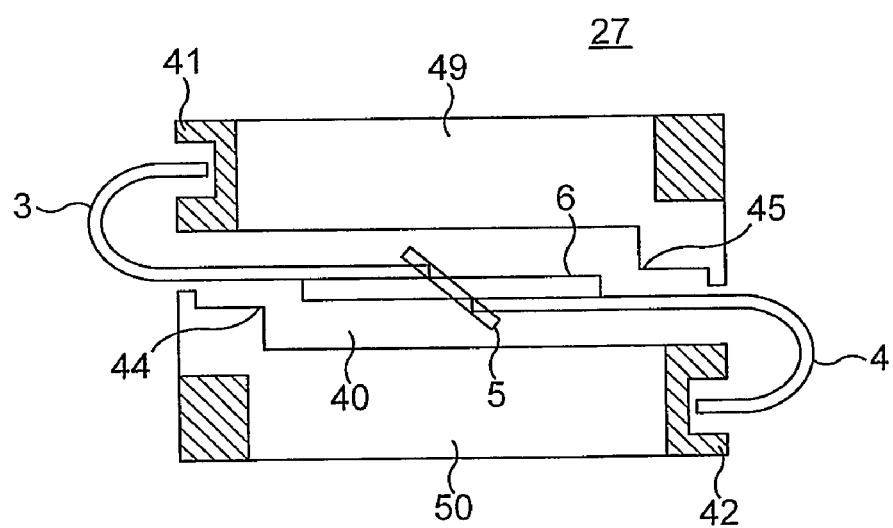
FIG. 4 shows a schematic representation of a clip in the inner shaft of the applicator.

The central region 40 holds the reaction 6 and base 5 portions of the clip. Generally, the reaction portion 6 of a clip is held approximately along the horizontal axis of the central region 40, extending across the width of the central region between the two guide rails 41, 42. The base portion 5 of the clip is generally offset from the horizontal, so as to help offset the arms of the clip above and below the reaction portion 6. FIG. 4 shows a schematic representation of a clip in the inner shaft 27 of the applicator 20. The reaction portion 6 may overlie, and thus to some extent be maintained horizontal by, diagonally opposed, inwardly projecting members 44, 45 provided on the corners of the central region 27 cross-section opposite to the two guide rails 41, 42.

Figure 5:
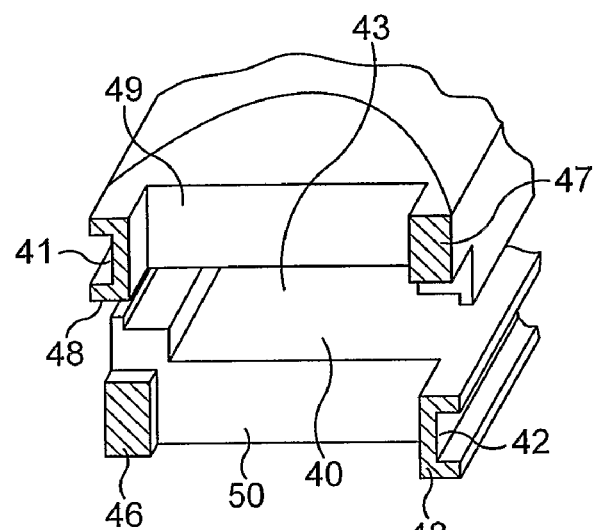
FIG. 5 shows a release zone of the applicator.

In order to place a clip effectively across a body passageway, the release zone 43 (front-most part) of the applicator is shaped to accommodate the body passageway securely in the optimal position for ligation. As shown in FIG. 5, the two outer guide rails 41, 42, one for each limb 3, 4 of the clip, extend beyond the end of the central region 40, forming two prongs projecting on opposite corners of the inner shaft 27. The upper bar 49 of the inner shaft 27 has a redundant, non-grooved bar (prong) 47 extending opposite and parallel to the guide rail 41. A further redundant, non-grooved bar (prong) 46 is similarly provided on the lower bar 50 of the inner shaft 27. Thus, two diagonally opposed, redundant, non-grooved bars 46, 47 are provided on the remaining two corners of the shaft, so that four prongs extend beyond the end of the central region 40. These form the release zone 43 and enable the body passageway to be located up against the reaction portion 6 of the clip and directly between the two limbs 3, 4 of the clip before it is released. The end face 48 of each guide rail 41, 42 in the release zone 43 forms a perpendicular, rectangular opening, to help ensure the smooth release of the clip. Otherwise, the clip may not be evenly released.

Thus, the body passageway is advanced well inside the release zone 43, so that it lies in-between the limbs 3, 4 of the clip and across the reaction portion 6. When the clip is released, the limbs 3, 4 automatically fold inwards under the inherent biassing force into the closed position, securely gripping and occluding the body passageway between the limbs 3, 4 and the reaction portion 6 of the clip. As the applicator is subsequently withdrawn from the body passageway, the base portion 5 of the clip is released from the central region 40 of the inner shaft 27 of the applicator. The shape of the release zone also helps to ensure that the applied clip does not cut, puncture or penetrate the body passageway or any surrounding structures.

Operation of the applicator will now be described.

The clips 1 are advanced along the inner shaft 27 of the applicator 20 by the outer sliding tube 25. As shown in FIG. 2, the outer sliding tube 25 surrounds the inner shaft 27 and has a flared section 51 at its rear end for abutting against the sprung stop-cap 26.

Figure 6:
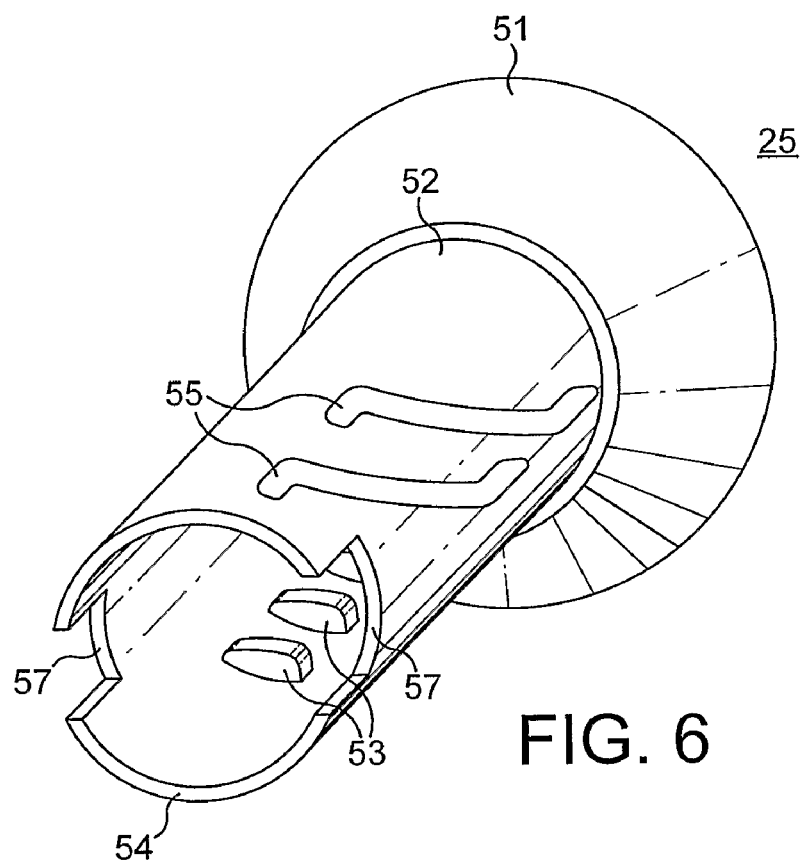
FIG. 6 shows a perspective view of an outer sliding tube of the applicator.

FIG. 6 shows a perspective view of the outer sliding tube (outer movable member) 25. As can be seen, it comprises a hollow cylindrical body 52 having the flared section 51 at its rear end. Clip-stops 53, in the form of small inward projections, are provided along the inside of the cylindrical body 52, and are separated in the longitudinal direction of the cylinder. This figure shows a somewhat shortened view of the outer sliding tube; as can be seen in FIG. 2, for example, the cylindrical body 52 extends for some distance between the clip stops 53 and the flared section 51. Preferably, each clip stop comprises two opposed projections, facing each other across the hollow cylinder of the tube.

Figure 7:
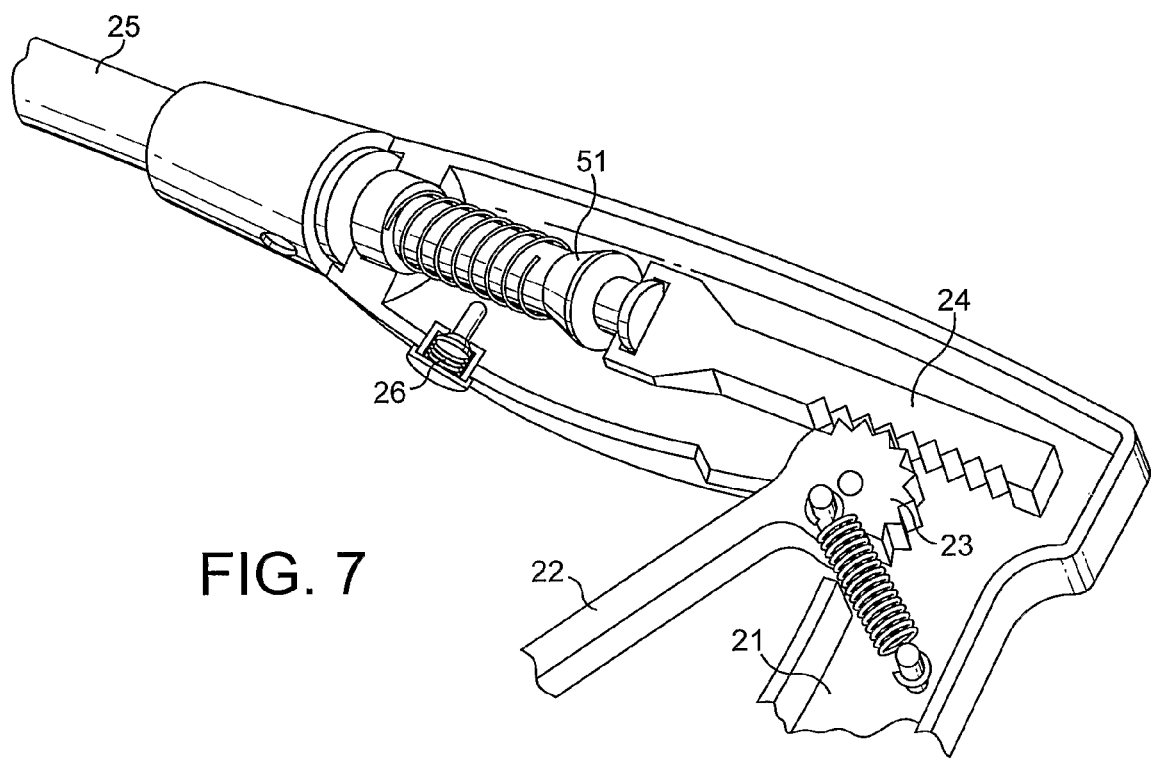
FIG. 7 shows the outer sliding tube of the applicator in an un-activated position.

FIGS. 2 and 7 show the outer sliding tube of the applicator in an un-activated position. When the trigger 22 is actuated and moved to trigger position A (FIG. 2), the outer sliding tube 25 is pushed forwards so that the flared section 51 at the rear end of the outer sliding tube abuts against the sprung stop-cap 26. The front end 54 of the outer sliding tube is moved forwards towards the clip release zone 43. The outer sliding tube is moved forwards by means of the cog 23 and ratchet 24 as the trigger 22 is pulled back to position A (actuated).

During the movement of the outer sliding tube 25, the clip stops 53 provided on the inner surface of the tube cylinder 52 push the mounted clips 1 forward, in concert. When the trigger is moved to position A, the clips are each moved forwards by a distance slightly less than one stop amount, where one stop amount is the separation of adjacent clip stops, thereby moving the foremost clip to the release zone 43. The sprung stop-cap 6 ensures that the outer sliding tube 25 moves forwards by the correct distance by abutting against the flared section 51 of the outer sliding tube after the desired forward displacement. This desired forward displacement is set as the amount of forward movement of the ratchet 24 when the trigger 22 is moved to position A from its unactuated position. The separation of the clip stops 53 may be of the order of 15 mm.

Figure 8:
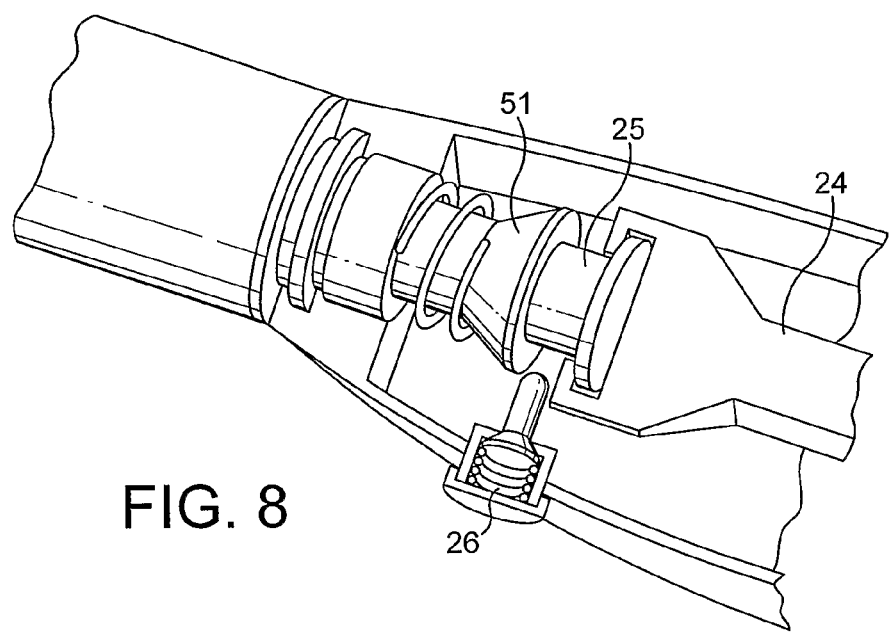
FIG. 8 shows the outer sliding tube in an activated position.

At this point, if the trigger 22 is further depressed, the ratchet 24 is moved further forwards and the flared section 51 of the outer sliding tube is forced beyond the sprung stop-cap 26, as shown in FIG. 8. This causes the clip stop 53 behind the foremost clip to push that clip into the release zone 43, off the inner shaft 27. In other words, the clip is pushed beyond the end of the central region (carriage) until the limbs 3, 4 are forward of their respective guide rails 41, 42, thus causing the clip 1 to be applied to the body passageway in the release zone 43 of the applicator 20. After this further forward displacement, the outer sliding tube 25 has moved forwards along the inner shaft 27 by a distance equal to the separation of the clip stops 53. Thus, each of the remaining clips is now positioned in the applicator at the point along the shaft previously occupied by its preceding clip before the trigger was actuated.

The front end of the outer sliding tube 25 is provided with indents 57 at the upper and lower portions of the cylinder. Thus, as the outer sliding tube moves forwards and pushes the foremost clip into the release zone, the body passageway to be encircled passes through the indents. Otherwise, if the indents were not provided, the front end of the outer sliding tube would dislodge the body passageway, and it would not be possible to apply a clip successfully.

At this stage, after the foremost clip has been applied, it is necessary to return the outer sliding tube 25 to its original position (that of FIGS. 2 and 7), so that the next clip may be applied. However, the outer sliding tube must be returned to its original position without disturbing the remaining clips, as each clip must move to the exact position of the preceding clip on actuating the applicator, in order to ensure that the foremost clip is always correctly positioned in the release zone for dispensing. In order to do this, the outer sliding tube 25, and thus the clip stops 53 also, are rotated so that the clip stops are no longer aligned with the mounted clips. Preferably, the outer sliding tube is rotated through about 90°.

Figure 9:
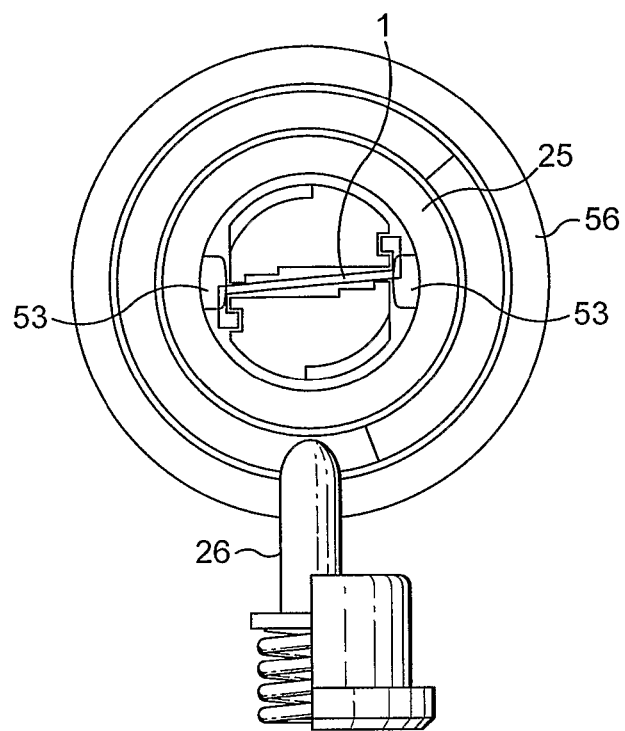
FIG. 9 shows a cross-section of the applicator, with the outer sliding tube at a first rotational position.
Figure 10:
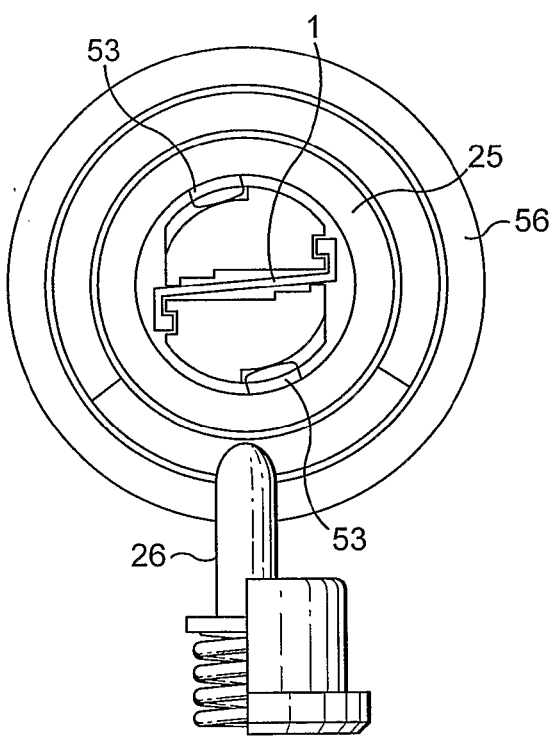
FIG. 10 shows a cross-section of the applicator, with the outer sliding tube at a second rotational position.

FIGS. 9 and 10 show a cross-section of the inner mechanism and outer sliding tube of the applicator, to illustrate the rotation. In FIG. 9, the clip stops 53 are aligned with the limbs 3, 4 of the clips 1 in the guide rails 41, 42 on the outside of the inner shaft 27. Thus, in this position, the clip stops 53 are able to move the clips 1 along the shaft 27 of the applicator, as they abut against the limbs 3, 4 of the clips. In FIG. 10, the outer sliding tube 25 has been rotated through 90°, so that the clip stops 53 are no longer aligned with the clips 1. Thus, in this configuration, it is possible to return the sliding tube 25 to its original position without disturbing (moving) the clips. Hence, as the trigger 22 is released, the sliding tube rotates and returns to the starting position.

The outer sliding tube 25 may be rotated by means of a manual swivel tube 56 provided around its circumference, i.e. it may be rotated manually by the surgeon after applying a clip. This is the embodiment depicted in FIGS. 9 and 10, where a manual swivel tube 56 is provided around the outer sliding tube 25.

Figure 11A:
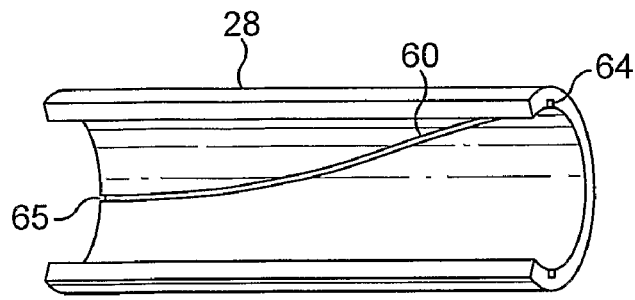
FIGS. 11A to C show the outer sliding tube and a casing in an embodiment of the applicator in which the outer sliding tube is rotated automatically.
Figure 11B:
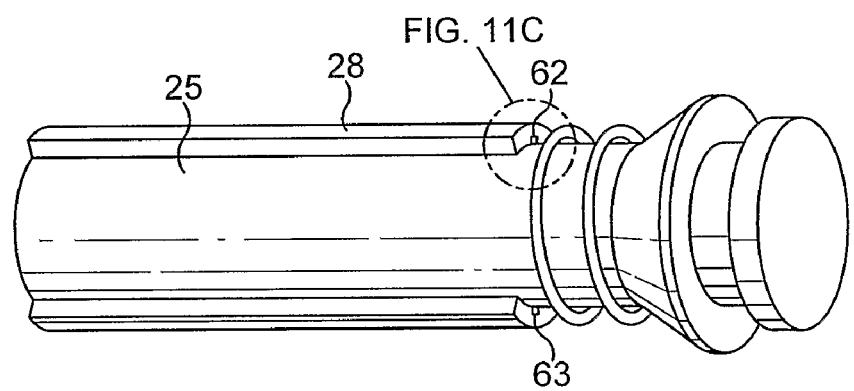
Figure 11C:
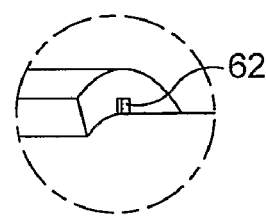
Figure 12:
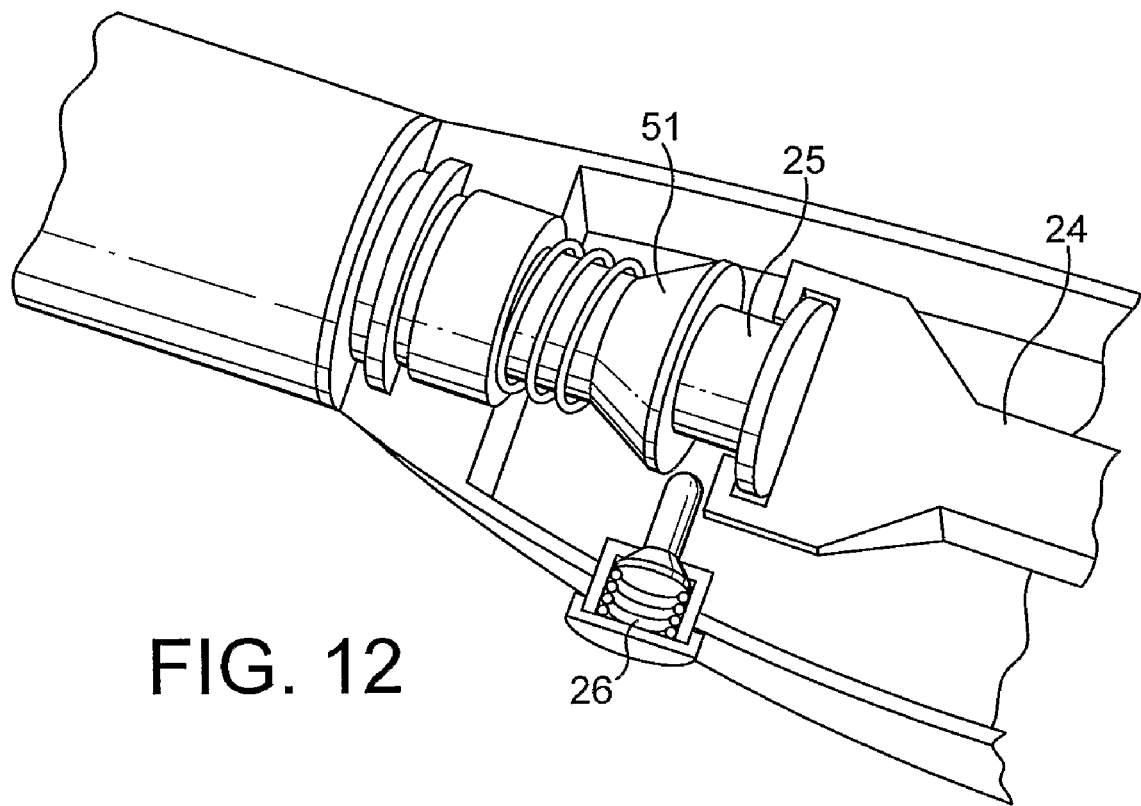
FIG. 12 shows the outer sliding tube engaging with the casing of FIGS. 11A to C.

Alternatively, the outer sliding tube may be rotated automatically in a spring-activated manner upon release of the trigger 22. FIGS. 11A to C and FIG. 12 show an embodiment of the applicator in which the outer sliding tube 25 is rotated automatically. As shown in the figures, a casing 28 is provided around the outer sliding tube 25 towards its rear end. A groove 60 is provided on the inner surface of the casing 28, as can be seen in FIG. 11A. This groove is curved, having a start position 64 and a finish position 65 approximately 90 degrees apart, about the shaft axis. A similar groove 61 may be provided on the opposite side of the inner surface of the casing 28. As shown in FIG. 11B, the outer surface of the outer sliding tube 25 is provided with a pinion (small outward projection) 62 aligned with the start position of the groove 60. If a second groove 61 is provided on the outer member, a further, matching pinion 63 is provided on the outer sliding tube accordingly. An enlarged section of a pinion and groove is shown in FIG. 11C.

According to this embodiment, in the unactuated position the outer sliding tube is at a rotational position equivalent to that shown in FIG. 10. In other words, the clip stops are not aligned with the limbs of the clips, but are positioned approximately 90 degrees from alignment. The pinions 62, 63 provided on the outer surface of the outer sliding tube are radially aligned with (but longitudinally displaced from) the clip stops 53. As the trigger 22 is moved to position A, causing the outer sliding tube 25 to be displaced forwards by means of the cog 23 and ratchet 24, the pinions 62, 63 provided on the outer surface of the outer sliding tube engage with the grooves 60, 61 in the inner surface of the casing. Thus, as the outer sliding tube moves further forwards, the pinions follow the line of the grooves through 90 degrees, causing the outer sliding tube to rotate through 90 degrees also. Therefore, the clip stops are rotated through ninety degrees so that they are subsequently aligned with the limbs of the clips, i.e. along the horizontal plane of the clips. The clips can then be displaced forwards towards the release zone of the applicator by the desired amount, by setting the travel amount of the trigger accordingly.

After a clip has been dispensed, and the trigger has been released, the trigger returns to the unactuated (resting) position by means of spring-loading. This causes the outer sliding tube to be withdrawn from the release zone 43 of the applicator by the cog and ratchet mechanism. As the outer sliding tube is withdrawn, the pinions 62, 63 follow the grooves provided in the inner surface of the casing 28, thus causing the outer sliding tube and the clip stops also to rotate back through 90 degrees, so that the clip stops are no longer aligned with the limbs of the clips. This enables the outer sliding tube to be withdrawn (returned to its original position) without disturbing the clips from their respective positions.

Preferably, the casing 28 extends along the length of the outer sliding tube 25, towards the front end of the outer sliding tube, thus encircling both the outer sliding tube 25 and the inner shaft 27 also. The casing is connected to the spaced bars 49, 50 of the inner shaft 27. The casing is a hollow cylinder having fasteners disposed on its inner surface in the region of the inner shaft. These fasteners pass through slits 55 in the outer sliding tube and engage with the sides of the bars 49, 50 (away from the guide rails 40, 41) of the inner shaft 27. In this manner, the casing holds the component bars 49, 50 of the inner shaft together in the desired configuration, with a space (central region) between the bars. The slits (slots) 55 in the outer sliding tube, through which the fasteners pass, are long enough to enable the outer sliding tube to move through its full desired displacement along the shaft of the applicator without the fasteners obstructing its movement. The slits may be curved to take account of any rotational movement of the outer sliding tube. The curvature of the slits matches the path followed by the pinions 62, 63 through their grooves 60, 61, to enable the outer sliding tube to rotate freely.

FIG. 13 shows the applicator with the casing 28 provided around the outer sliding tube. Thus, the casing stabilises the upper 49 and lower 50 bars of the inner shaft 27, and provides protection to the applicator structure as a whole. It also presents a smooth outer surface to any surrounding anatomical structures. Alternatively, instead of providing a single casing 28, separate casings may be provided towards the front and rear ends of the outer sliding tube; the former for holding the inner shaft 27 together, and the latter for providing the grooves 60, 61 to enable the outer sliding tube to rotate.

A two-stage procedure is required in order to load the nitinol clips, as they are super-elastic at room temperature. In one method, firstly, a clip is cooled to approximately 5° C., whilst attached to a dedicated carrier, and is then loaded into the rear of the inner shaft 27 of the applicator. The dedicated carrier is a simple, straight handled applier or loader having a hollow end that fits onto the base portion of the clip to be loaded. The clip is in the open configuration as a result of having been cooled to 5° C., and is loaded into the inner shaft 27 of the applicator by twisting one limb 3 up onto the upper guide rail 41 of the upper bar 49 and twisting the other limb 4 down on to the lower guide rail 42 of the lower bar 50 of the shaft with the central portion of the clip accommodated in the central region 40 of the inner shaft between the two bars. The limbs of the clips are maintained in the open configuration within the maximum recoverable stress of the material, to ensure that the clips revert to the closed configuration on application. It is believed that a combination of relatively low temperature below body temperature (i.e. below the austenite start temperature $A_s$ and most preferably below the martensite finish temperature $M_f$, particularly below about 15° C.), and maintenance of the limbs in the open condition under some stress within the maximum recoverable stress provides the best conditions for obtaining an effective closure of the clips on release into an operating zone of a patient.

The loader has depth marks along its length, so that each clip can be loaded into the inner shaft of the applicator at the correct distance from the rear of the shaft to ensure accurate dispensing of the clips.

The clips can be loaded into the inner shaft 27 of the applicator through a loading aperture 58 provided in the outer sliding tube. The casing does not extend to the rear end of the inner shaft (if two casings are provided), or alternatively is provided with a loading aperture also.

The applicator can be reusable or disposable. In the case of a disposable, single-use, applicator, the loading of the clips will normally be done in the factory as part of the assembly process. In that case, the number of clips loaded is pre-set in the factory and corresponds to the number of clip stops incorporated in the particular design of the outer sliding tube and the length of the inner shaft. Any number of clips may thus be loaded, according to the specific clinical use of the applicator.

Loading of clips proceeds as follows. The bars (double carriages) are fixed to a bench-top clean room jig (not shown). This incorporates eight hold points (two [front and back] on each side of each carriage). The clips are separately cooled to around 5 EC, whilst attached to a dedicated carrier. The clips are loaded into the rear of the carriages, to pre-set depths, in sequence. Next, front and rear temporary carriage clasp and spacer units are attached to the double carriages (bars 49, 50). These maintain the inter-carriage space, and hold the carriages together, with the contained clips. The double carriages are then removed from the jig, using the front clasp. They are introduced into the front aperture of the sliding tube. The carriages (and clips) are introduced offset by 90E to the clip-stops. The carriages (forming the inner shaft 27) are then rotated 90E clockwise to engage the clip-stops. The four fasteners are pressed home, to engage both carriages and fix them to the casing. Finally the front clasp-spacer is removed; the rear spacer remains in-situ, as a back stop.

The applicator is suitably provided in two main sections for assembly immediately before use; the first section comprises the barrel (comprising the outer sliding tube and casing) and handle-trigger-main-housing. The second section comprises the inner shaft 27, comprising the upper 49 and lower 50 bars (double carriages), which is loaded with the clips. The second section is assembled with the first by being introduced into the distal (front) end of the applicator barrel.

The sections are preferably readied in a clean room environment of the factory, prior to packaging and final sterilization using a nitinol-compatible sterilising system such as ethylene oxide. It is preferred that the applicator or sections is/are provided to be sterile, disposable, and contained within a theatre-ready (sterile, double-wrapped) blister pack.

Although the terms 'above' and 'below' have been used to describe the positions of the limbs of a surgical clip, and the positions of the guide rails in the applicator, these terms are not intended to be limited to a strict vertical orientation of these parts. Rather, they describe the arrangement of the limbs of the clip on opposite sides of the plane of the main portion of the clip, and the arrangement of the guide rails on opposite sides of the central region of the applicator shaft, whether or not the plane of the main portion of the clip and the central region of the shaft are aligned in a horizontal direction.

Although the embodiments described have used the out-of-plane C-shaped clip with counter-surface, it is clear that the applicator is not restricted to the use of such clamps but is of general use where it is desired to guide the ends of two clip legs along two lines or planes.

The foregoing broadly describes the invention without limitation to particular embodiments thereof. Variations and modifications as will be readily apparent to those of ordinary skill in this art are intended to be included withing the scope of this application and subsequent patent(s).

The invention claimed is:

1. An apparatus (20) for dispensing a surgical clip (1), the clip comprising a central portion (2) defining a plane and a pair of limbs (3, 4) extending from opposite sides of the central portion, one (3) of the limbs having a free end disposed forward, and above the plane, of the central portion (2) and the other (4) of the limbs having a free end disposed forward, and below the plane, of the central portion (2), the apparatus comprising:
   an inner shaft (27) on or in which the clip can be mounted with its limbs facing forwards; and
   an outer movable member (25) for displacing the clip along the longitudinal axis of the inner shaft;
   wherein the inner shaft (27) comprises a central region (40) for accommodating the central portion (2) of the clip, and a pair of opposed guide rails (41, 42) provided on opposite sides of the central region (40), one (41) of the guide rails being positioned above the central region to accommodate the one limb (3) and the other (42) of the guide rails being positioned below the central region to accommodate the other limb (4) of the clip,
   wherein the inner shaft (27) comprises an upper bar (49) and a lower bar (50) spaced apart from one another, the central region (40) being formed by the space between the bars, wherein said one (41) of the guide rails is provided on a side of the upper bar (49) and said other (42) of the guide rails is provided on a side of the lower bar (50), wherein each of the guide rails (41, 42) faces outwardly away from the central region (40).

2. An apparatus according to claim 1, wherein the upper bar (49) and the lower bar (50) are substantially identical.

3. An apparatus according to claim 1, wherein each of the guide rails (41, 42) is coated with titanium.

4. An apparatus according to claim 1, wherein the outer movable member (25) comprises a hollow cylindrical body (52).

5. An apparatus according to claim 1, wherein the outer movable member (25) can be rotated about its longitudinal axis by means of a manual swivel tube (56).

6. An apparatus according to claim 1, further comprising a trigger (22) for actuating the outer movable member (25) to displace the clip (1).

7. An apparatus according to claim 1, wherein the guide rails (41,42) are diagonally opposed.

8. An apparatus according to claim 1, when loaded with one or more surgical clip (1) comprising a central portion (2) defining a plane and a pair of limbs (3, 4) extending from opposite sides of the central portion, one (3) of the limbs having a free end disposed forward, and above the plane, of the central portion (2) and the other (4) of the limbs having a free end disposed forward, and below the plane, of the central portion (2).

9. An apparatus according to claim 1, wherein the guide rails (41,42) are arranged to hold the limbs (3,4) of the clip splayed and under a stress within the maximum recoverable stress of the clip material.

10. An apparatus according to claim 1, wherein some or all of the components are made of a medical-grade polymer.

11. An apparatus according to claim 10, wherein the polymer is Delrin.

12. An apparatus according to claim 1, said one (41) of the guide rails is formed by a longitudinal channel provided between a rear end and a front end of the upper bar (49), and said other (42) of the guide rails is formed by a longitudinal channel provided between a rear end and a front end of the lower bar (50).

13. An apparatus according to claim 12, said one (41) of the guide rails extends beyond the front end of the upper bar (40) and the said other (42) of the guide rails extends beyond the front end of the lower bar (50).

14. An apparatus according to claim 12, wherein each of the guide rails (41, 42) has a substantially rectangular cross-section enclosed on three sides.

15. An apparatus according to claim 14, wherein each of the guide rails (41, 42) has a front end (48) having a rectangular opening perpendicular to the longitudinal axis of the inner shaft (27).

16. An apparatus according to claim 12, wherein each of the upper (49) and lower (50) bars has a prong (47, 46) provided at its front end on a side opposite to its respective guide rail (41, 42) and projecting parallel to its respective guide rail.

17. An apparatus (20) for dispensing a surgical clip (1), the clip comprising a central portion (2) defining a plane and a pair of limbs (3, 4) extending from opposite sides of the central portion, one (3) of the limbs having a free end disposed forward, and above the plane, of the central portion (2) and the other (4) of the limbs having a free end disposed forward, and below the plane, of the central portion (2), the apparatus comprising:
   an inner shaft (27) on or in which the clip can be mounted with its limbs facing forwards; and an outer movable member (25) for displacing the clip along the longitudinal axis of the inner shaft;

wherein the inner shaft (27) comprises a central region (40) for accommodating the central portion (2) of the clip, and a pair of opposed guide rails (41, 42) provided on opposite sides of the central region (40), one (41) of the guide rails being positioned above the central region to accommodate the one limb (3) and the other (42) of the guide rails being positioned below the central region to accommodate the other limb (4) of the clip, wherein the outer movable member (25) comprises a hollow cylindrical body (52), wherein clip stops (53) are provided along the inside of the cylindrical body (52) of the outer movable member (25).

18. An apparatus according to claim 17,
wherein each of the clip stops (53) comprises two opposed projections.

19. An apparatus according to claim 17,
wherein the clip stops (53) are separated in the longitudinal direction of the cylindrical body (52).

20. An apparatus according to claim 17,
wherein a loading aperture (58) is provided in the cylindrical body (52) of the outer movable member (25).

21. An apparatus according to claim 17,
wherein the cylindrical body (52) of the outer movable member (25) has opposed indents (57) provided at a first, front end.

22. An apparatus according to claim 17,
wherein the outer movable member (25) can be rotated automatically about its longitudinal axis as it is displaced along the longitudinal axis of the inner shaft (27).

23. An apparatus according to claim 22,
wherein a casing (28) is provided around the outer movable member (25) towards the second end thereof, the casing (28) having at least one curved groove (60, 61) in its inner surface, and the outer movable member being provided with at least one pinion (62, 63) in its outer surface, the at least one pinion matching the at least one curved groove.

24. An apparatus according to claim 23,
wherein the at least one curved groove (60, 61) has a start position (64) and a finish position (65) provided approximately ninety degrees apart with respect to the longitudinal axis of the inner shaft (27).

25. An apparatus according to claim 23,
wherein the at least one pinion (62, 63) provided on the outer surface of the outer movable member (25) is aligned radially with the clip stops (53).

26. An apparatus according to claim 17,
wherein the cylindrical body (52) of the outer movable member (25) has a flared section (51) provided towards a second, rear end.

27. An apparatus according to claim 26,
wherein the displacement of the outer movable member (25) along the longitudinal axis of the inner shaft (27) is controlled by a sprung stop-cap (26) which abuts against the flared section (51) of the outer movable member.

28. An apparatus (20) for dispensing a surgical clip (1), the clip comprising a central portion (2) defining a plane and a pair of limbs (3, 4) extending from opposite sides of the central portion, one (3) of the limbs having a free end disposed forward, and above the plane, of the central portion (2) and the other (4) of the limbs having a free end disposed forward, and below the plane, of the central portion (2), the apparatus comprising:

an inner shaft (27) on or in which the clip can be mounted with its limbs facing forwards; and an outer movable member (25) for displacing the clip along the longitudinal axis of the inner shaft;

wherein the inner shaft (27) comprises a central region (40) for accommodating the central portion (2) of the clip, and a pair of opposed guide rails (41, 42) provided on opposite sides of the central region (40), one (41) of the guide rails being positioned above the central region to accommodate the one limb (3) and the other (42) of the guide rails being positioned below the central region to accommodate the other limb (4) of the clip, wherein the inner shaft (27) comprises an upper bar (49) and a lower bar (50) spaced apart from one another, the central region (40) being formed by the space between the bars, further comprising a casing provided around the inner shaft (27) and outer movable member (25), the casing being fastened to the upper (49) and lower (50) bars of the inner shaft by fasteners.

29. An apparatus according to claim 28,
wherein the outer movable member (25) is provided with slits through which the fasteners can pass.

* * * * *